United States Patent [19]
Yamamoto et al.

[11] Patent Number: 5,255,562
[45] Date of Patent: Oct. 26, 1993

[54] MEASUREMENT OF INTERFACIAL STRENGTH OF A COMPOSITE MATERIAL

[75] Inventors: Yasunori Yamamoto, Nagaokakyo; Tsukasa Nishimura, Kyoto, both of Japan

[73] Assignee: Shimadzu Corporation, Japan

[21] Appl. No.: 957,733

[22] Filed: Oct. 7, 1992

[30] Foreign Application Priority Data

Jan. 24, 1992 [JP] Japan .................................. 4-034171

[51] Int. Cl.$^5$ .......................... G01D 1/02; G01N 3/24
[52] U.S. Cl. .......................................... 73/160; 73/78; 364/508
[58] Field of Search ................. 73/160, 788, 789, 781; 364/508

[56] References Cited

U.S. PATENT DOCUMENTS

| | | | |
|---|---|---|---|
| 4,635,471 | 1/1987 | Rogers et al. | 73/78 X |
| 4,807,465 | 2/1989 | Botzolakis et al. | 73/78 |
| 4,942,768 | 7/1990 | McRae | 73/789 |
| 4,947,341 | 8/1990 | Shine | 364/508 |

*Primary Examiner*—Daniel M. Yasich
*Attorney, Agent, or Firm*—Heller, Ehrman, White & McAuliffe

[57] ABSTRACT

Interfacial strength of a composite material between its fibers and matrix is measured by observing a sample material through a microscope, measuring the diameter of selected one of the fibers by moving indicators in the field of vision of the microscope, applying pressure on the selected fiber by means of an indentator and measuring both the displacement of the indentator and the load on the fiber, and thereby obtaining a curve between the indentator displacement and the square root of the load. The curve has a straight portion and the point at which the curve begins to deviate from the straight portion is determined. The load value corresponding to this point is used to calculate debonding and sliding interfacial shear strengths of the material according to given formulas.

17 Claims, 3 Drawing Sheets

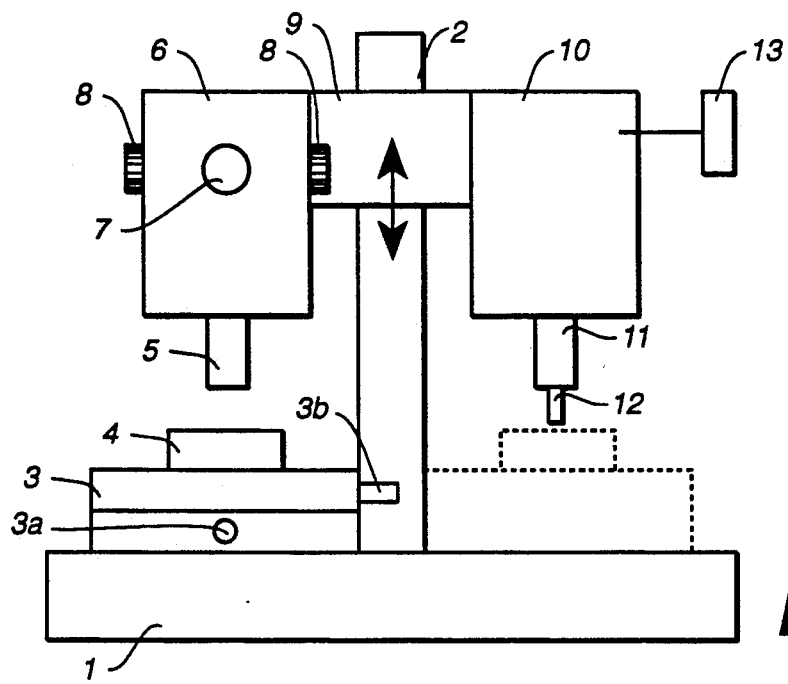
FIG._1
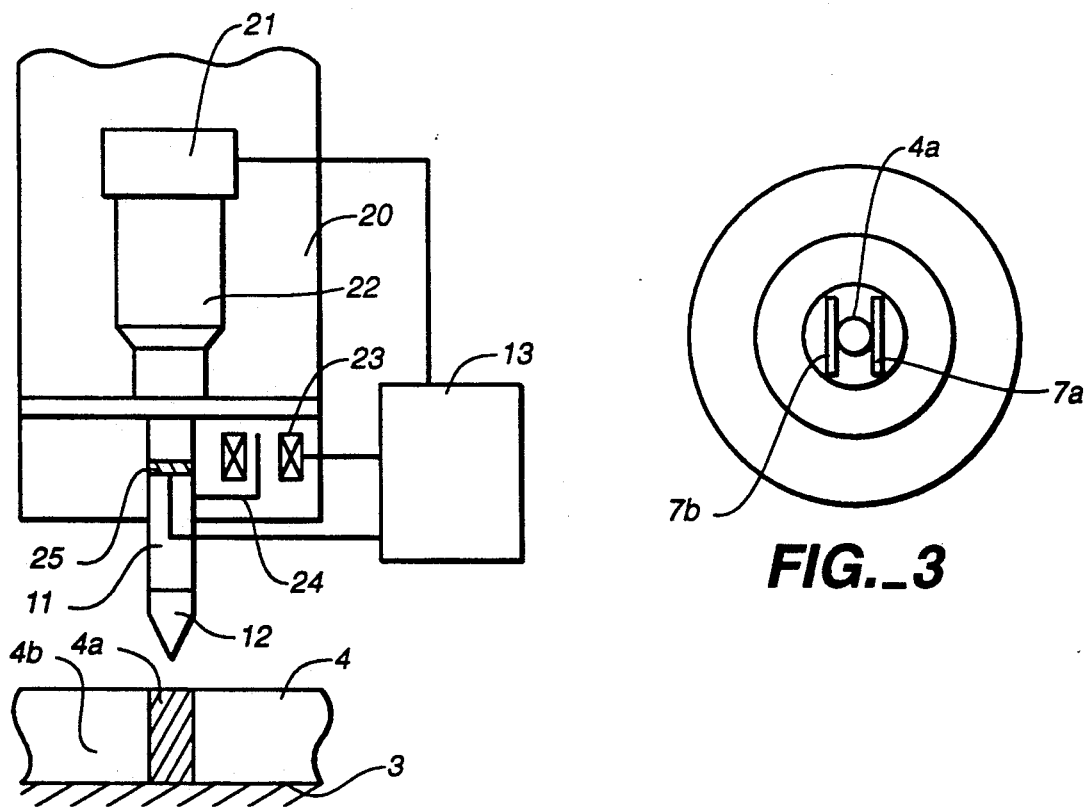
FIG._2
FIG._3

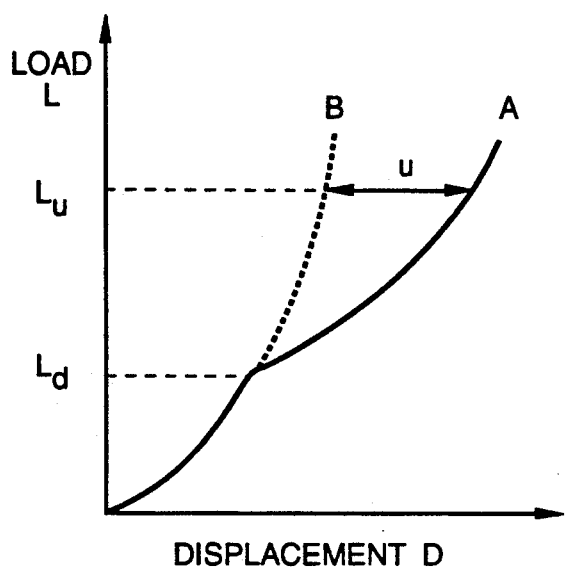
FIG._4
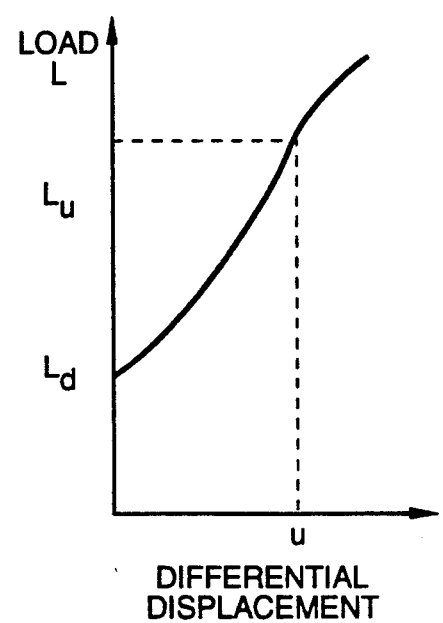
FIG._5
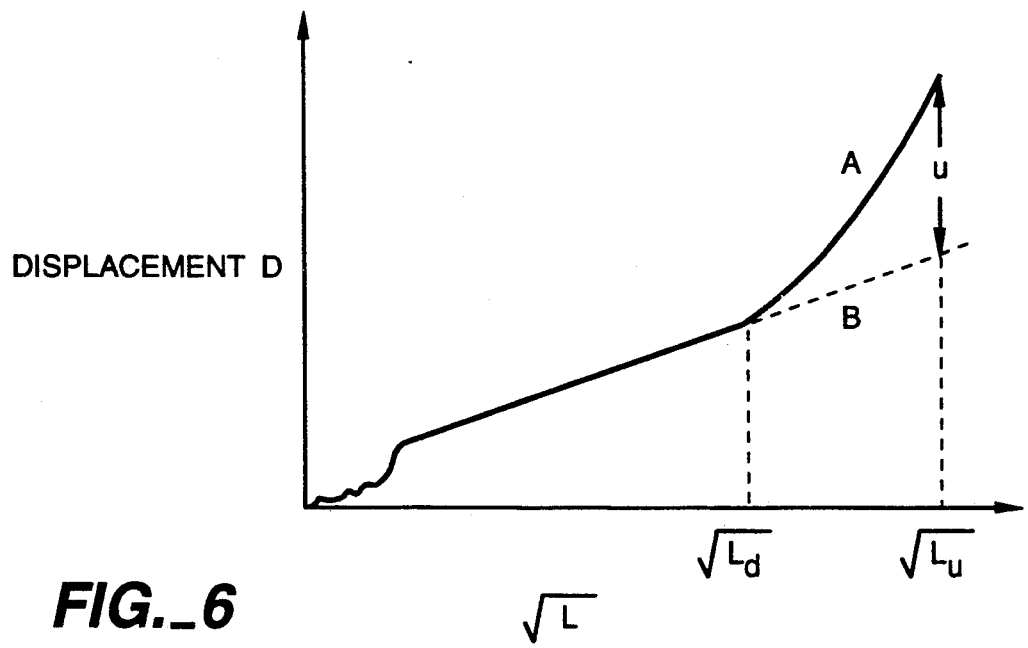
FIG._6

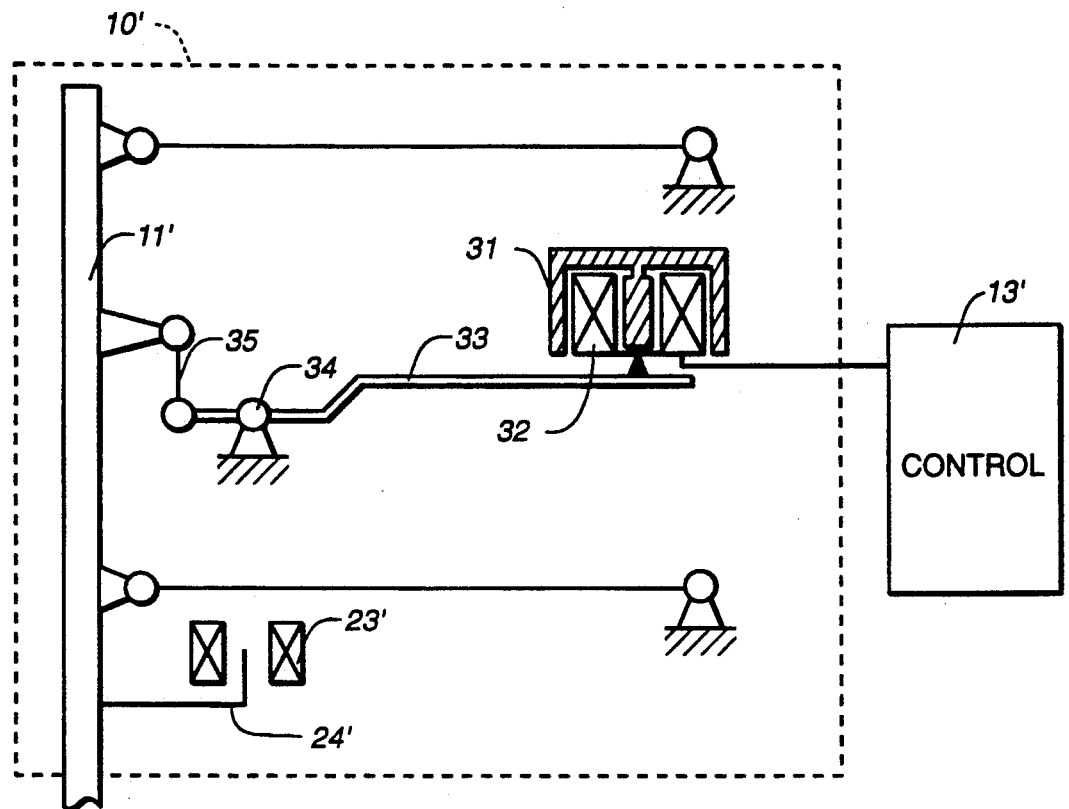
FIG._7
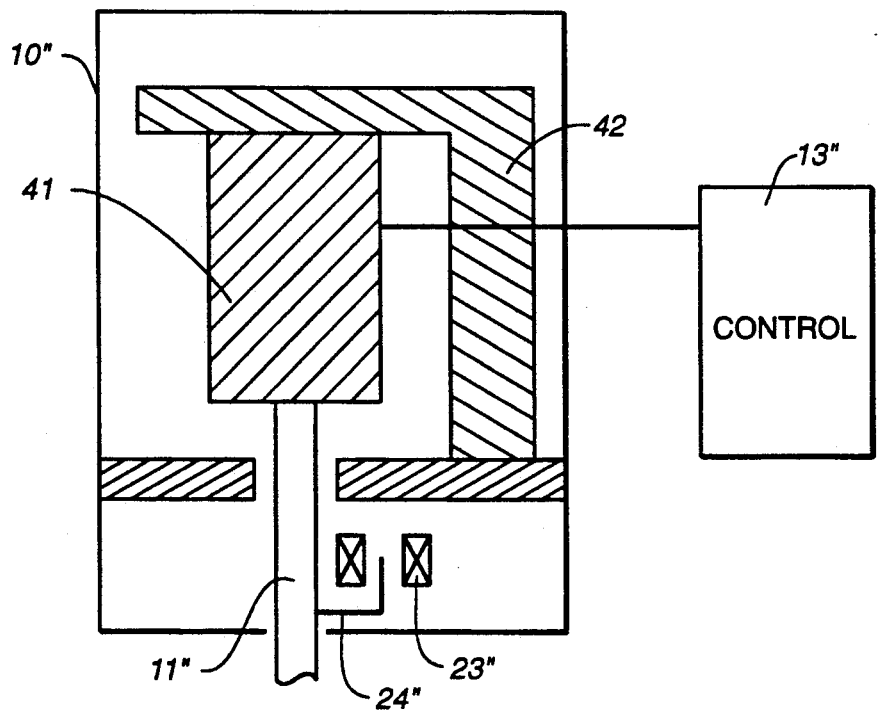
FIG._8

MEASUREMENT OF INTERFACIAL STRENGTH OF A COMPOSITE MATERIAL

BACKGROUND OF THE INVENTION

This invention relates to a method of evaluating the interfacial strength of a composite material at a boundary between its fiber and matrix. This invention relates also to an apparatus for using such a method.

Composite materials with reinforcing fibers dispersed within matrix are widely in use in various fields of industrial applications such as automobiles, airplanes, tanks and concrete. For evaluating the interfacial strength between the fibers and the matrix of such a material, it is necessary to apply a force on a fiber in order to cause a separation. Since the fibers in such materials are usually very thin with a diameter on the order of 10~150 microns, however, use must be made of an indentator with a sharp tip. Since such an indentator penetrates the fiber while pushing it, what is actually being measured is the total displacement of the indentator, including the distance by which the fiber is penetrated by the sharp tip of the indentator. In order to obtain only that portion of the displacement of the indentator at the interface between the fibers and the matrix, therefore, the distance of penetration by the indentator must be subtracted from the measured total displacement.

In order to determine the distance of penetration by an indentator, it has been known to preliminarily provide a correction curve by using a test sample with a very large interfacial strength between its fibers and matrix and to make use of such a curve to make corrections on measured values. It is cumbersome, however, to keep making reference to such a correction curve in order to obtain a desired displacement value at the interfacial boundary. Moreover, there are situations where a sample cannot be manufactured with a satisfactorily large interfacial strength. In such a situation, it is impossible to prepare a correction curve needed for the method. Furthermore, there has not been available any apparatus designed specifically for the measurement of interfacial strength of composite materials. It seems to have been a common practice among some researchers to make changes on a commercially available instrument for measuring hardness, but such a make-shift instrument is not easy to operate, and use was commonly made of an average value of fiber diameters rather than the diameter of the selected fiber which is actually tested. As a result, fluctuations were large, and the conclusions obtained by such prior art methods were not highly reliable.

In view of the above, it is a general object of the present invention to provide an improved method of measuring interfacial strength of a composite material accurately.

It is a more specific object of the present invention to provide such a method which does not require a sample to be manufactured with a large interfacial strength for preparing a correction curve but is able by a single test to determine the critical value of load at which separation of fibers starts at the interfacial boundary.

It is still another object of the present invention to provide an apparatus which makes use of such a method for the measurement of interfacial strength of a composite material.

SUMMARY OF THE INVENTION

A method embodying the present invention, with which the above and other objects can be accomplished, may be characterized as comprising the steps of applying a load on a selected one of reinforcing fibers by means of an indentator, measuring the displacement of the indentator while increasing the load thereon to thereby obtain a characteristic curve representing the relationship between the square root of the load and the displacement. Since the penetration of the indentator into the fiber should be proportional to the square root of the load from the definition of its hardness, the deviation from a straight line of the curve representing this measured relationship represents the portion of the indentator displacement at the interfacial boundary between the fibers and the matrix of the material being tested. The value of the load at which this deviation starts is the critical load at which the separation of fibers is considered to have started.

An apparatus embodying the present invention, with which the method described above can be used, may be characterized as comprising a selecting means for selecting one of the reinforcing fibers from a sample of composite material, a diameter-measuring means for measuring the diameter of the selected fiber, an indentator for pressing the fiber, a loading means for applying a load on the indentator, a load-measuring means for measuring the magnitude of the load being applied to the fiber by the indentator, a displacement-measuring means for measuring the displacement of the indentator as the selected fiber is pressed thereby, and a calculating means for calculating the surface shear strength of the fibers from measured data. This apparatus is adapted to calculate the interfacial shear strength of fibers while applying a load on the indentator and measuring the corresponding displacement of the indentator.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic front view of an apparatus embodying the present invention to show its general structure;

FIG. 2 is a schematic sectional front view of the loading unit, showing also its functional connection to the control unit;

FIG. 3 is a sketch of the field of vision of the microscope;

FIGS. 4, 5 and 6 are graphs for schematically showing the basic principle and actual method of obtaining data from which the interfacial shear strengths can be calculated according to the present invention;

FIG. 7 is a schematic sectional front view of another loading unit embodying the present invention, having an electromagnetic indentator-driving means controlled by a control unit; and FIG. 8 is a schematic sectional front view of still another loading unit embodying the present invention, having a piezoelectric indentator-driving means controlled by a control unit.

DETAILED DESCRIPTION OF THE INVENTION

As shown schematically in FIGS. 1 and 2 which illustrate an apparatus embodying the present invention, a base 1 supports a support column 2 for vertically moving its loading unit 10 upward and downward and a sample table 3 with as so-called X-Y stage (not shown) one side of the support column 2. The X-Y stage may be of a known kind comprising a pair of plates which can be moved with respect to each other by rotating micrometer heads 3a and 3b such that one can slide in one direction and the other in a perpendicular direction, enabling the user to move two-dimensionally a sample placed thereon. A sample 4 of a composite material with reinforcing fibers 4a dispersed in a matrix 4b is placed on top of the X-Y stage. A microscope 6 has its objective lens 5 disposed above the sample table 3 such that the sample can be observed through its eye piece 7. As shown in FIG. 3, indicators 7a and 7b are adapted to appear in the field of vision of the microscope 6. Knobs 8 shown in FIG. 1 are for moving these indicators 7a and 7b.

The microscope 6 and the loading unit 10 are attached to a support table 9 which can be moved vertically upward and downward along the support column 2. The loading unit 10 includes a vertically extending rod 11 with an indentator 12 attached at the bottom, and is functionally connected to a control unit 13 for the control of measurements. The control unit 13 is of a known kind generally adapted to carry out many functions including transmitting signals to apparatus, receiving signals from various sensors and detectors, performing analog-to-digital conversion of such received signals and carrying out various numerical calculations. As shown in FIG. 2, the loading unit 10 contains within its frame 20 a motor 21 for moving the indentator 12 up and down, a micrometer 22 adapted to have its spindle move linearly downward without rotating it, a position sensor 23 of a known kind with a core rod 24 for detecting vertical displacement of the indentator 12, and a load sensor (such as a load cell) 25 for measuring the load on the indentator 12. The sample table 3 can slide between a left-hand position (with reference to FIG. 1 and shown in solid lines therein) below the microscope 6 and a right-hand position (shown by broken lines in FIG. 1) below the indentator 12. The sliding mechanism for the sample table 3 is adapted such that the point on the sample table 3 which is positioned at the center of the field of vision of the microscope 6 by the user as described below when the sample table 3 is at the left-hand position will automatically come to the position directly below the indentator 12 when the sample table 3 is moved to the right-hand position.

For the measurement by this apparatus, the sample 4 on the X-Y stage is observed first through the microscope 6, and a fiber to be pushed for testing is selected by the user and moved to the center of the field of vision of the microscope 6. The diameter of the selected fiber is measured by rotating the knobs 8 to move the indicators 7a and 7b so as to sandwich it exactly therebetween as shown in FIG. 3. Thereafter, the sample table 3 is caused to slide to the right-hand position below the indentator 12. Since the selected fiber 4a, of which the diameter has been measured as described above, is directly below the indentator 12, a command signal is outputted from the control unit 13 to activate the motor 21, causing the micrometer 22 to move downward. The indentator 12 is thereby lowered and pushes the selected fiber 4a downward. The load L on the fiber 4a and the displacement of the indentator 12 are measured by the sensors 23 and 25. The load L will be constant, representing the weight of the indentator 12 itself before the indentator 12 comes into contact with the sample 4, increasing suddenly when the indentator 12 touches the sample 4. Displacement D of the indentator 12 will be herein measured from this point. In other words, the zero-point of the displacement D is taken at the point where the load L increases suddenly as the indentator 12 touches the sample 4.

The relationship between the load L and the indentator displacement D, as defined above, is as shown in FIG. 4 by Curve A for a typical composite material. If its interfacial strength were extremely strong, the relationship between the load L and the indentator displacement D for such an idealized material would be as shown by Curve B, with Curves A and B coinciding where the load L is smaller than a certain critical value hereinafter referred to as the "debonding load $L_d$". For a load such as $L_u$ greater than $L_d$, the difference in indentator displacement between Curve A and B will be herein referred to as the differential displacement and denoted by u, as shown in FIG. 4. FIG. 5 is a graph, derived from Curves A and B in FIG. 4, between the load L and the differential displacement u. Curves A and B in FIG. 4 show that indentator displacement D is essentially due to the penetration of the indentator 12 into the fiber 4a before the value of the load L reaches $L_d$ at which the fiber 4a begins to separate from the matrix 4b. Since the distance D by which the indentator 12 with a load of L penetrates the fiber 4a is related to the hardness H of the fiber 4a according to the formula $H = aL/D^2$ where a is a constant depending on the indentator, one obtains:

$$D = (aL/H)^{\frac{1}{2}}. \qquad \text{Formula (1)}$$

In other words, the indentator displacement D due only to its penetration into the fiber 4a should be proportional to the square root of load, and this relationship should appear as a straight line in a graph between D and square root of L (that is, $\sqrt{L}$).

FIG. 6 is such a graph showing the relationship between D and $\sqrt{L}$ corresponding to Curves A and B of FIG. 4. In FIG. 6, Curves A and B are nearly straight for load value less than $L_d$. Irregularities near the origin of the graph may be interpreted as representing the surface roughness of the sample 4. As explained above with reference to FIG. 4, the vertical separation between the two curves in FIG. 6, or the differential displacement u, represents the portion of the indentator displacement D at the interfacial boundary, that is, the difference between the total indentator displacement and the distance of penetration by the indentator 12 into the fiber 4a when the load $L_u$ is greater than the debonding load $L_d$.

According to a method of measurement embodying the present invention, the apparatus of FIGS. 1 and 2 is used to measure and record mutually corresponding values of the load L and the indentator displacement D. If the results are plotted as a relationship between the square root of load ($\sqrt{L}$) and D, the graph thus obtained will generally look like Curve A in FIG. 6 with a substantially straight portion extending to a certain point, deviating therefrom for loads and displacements beyond this point. This point is identified as the debonding point and the value of the load corresponding to this point ($=L_d$) is identified. A value of differential displacement u corresponding to a certain load ($=L_u$) greater than $L_d$ is also obtained. The debonding shear strength $\tau_d$ and the sliding shear strength $\tau_s$ are calculated (say, by the control unit 13) from these values as follows:

$$\tau_d = \alpha L_d / 2\pi R^2, \text{ and} \qquad \text{Formula (2)}$$

$$\tau_s = L_u^2 / (4\pi^2 R^3 E_f \mu) \qquad \text{Formula (3)}$$

where
$$\alpha^2 = 2E_m / \{E_f(1+\nu_m)^2 \ln(1/\sqrt{B})\}, \qquad \text{Formula (4)}$$

E is the elastic modulus, $\nu$ is the Poisson's ratio, R is the radius of the fiber, B is the bulk modulus of the fiber, and the subscripts m and f respectively refer to the matrix and the fibers.

As can be understood from the formulas given above, shear strength depends heavily on the radius of the fiber. Since an actually measured value of the diameter, rather than an average value, is used in the calculation according to the present invention, the result obtained by the method of the present invention is expected to be far more reliable. The present invention, furthermore, eliminates the need to go through the trouble of manufacturing a test sample with high surface strength and makes it possible to carry out evaluation of different kinds of composite materials easily and accurately.

Although the present invention has been described above by way of only one embodiment, it was intended to be illustrative, and not as limiting the scope of the invention. The indentator 12, for example, need not be raised or lowered by means of a motor as described above with reference to FIG. 2. FIG. 7 shows another indentator-driving mechanism for another loading unit 10', characterized by electro magnetic means for controlling the motion of the indentator (not shown), including a combination of a permanent magnet 31 and a coil 32 serving together as a driving unit, the coil 32 being placed within the magnetic field of the permanent magnet 31. The coil 32 is attached to one end of a lever 33, and the current therethrough is controlled by a control unit 13'. The other end of the lever 33, opposite the coil 32 across its fulcrum 34, is attached to a rod 11' through a plate spring 35 such that the vertical motion of the rod 11', and hence also that of the indentator, can be controlled by the control unit 13'. FIG. 8 shows still another indentator-driving mechanism for still another loading unit 10', characterized by the use of a piezoelectric element 41 attached to a supporting bracket 42. A control unit 13'' is adapted to control the current supplied to the piezoelectric element 41 to thereby control the vertical motion of a rod 11''. In FIGS. 7 and 8, other components which are substantially the same as those shown in, and explained with reference to, FIG. 1 are indicated by the same numerals.

In summary, all such modifications of variations of the disclosures given above, that may be apparent to persons skilled in the art, are intended to be included within the scope of the invention.

What is claimed is:

1. An apparatus for measuring interfacial strength of a composite material, said apparatus comprising:
    selecting means for allowing a user to select a reinforcing fiber within a sample of said composite material;
    diameter-measuring means for measuring the diameter of said selected fiber;
    an indentator for compressing said selected fiber;
    loading means for applying a load on said indentator and thereby causing said indentator to compress said selected fiber;
    load-measuring means for measuring said load;
    displacement-measuring means for measuring the magnitude of displacement of said indentator; and
    calculating means for calculating surface shear strengths of said fiber from load and displacement data obtained by said load-measuring and displacement-measuring means and the diameter of said selected fiber measured by said diameter-measuring means.

2. The apparatus of claim 1 wherein said selecting means include a slidably movable table for carrying said sample thereon and a microscope disposed above said table.

3. The apparatus of claim 1 wherein said diameter-measuring means include a microscope with indicators and indicator-moving means for moving said indicators selectively towards or away from each other.

4. The apparatus of claim 1 wherein said indentator has a sharp tip pointing downward, said sharp tip being adapted to compress said selected fiber exclusively.

5. The apparatus of claim 1 wherein said loading means include a motor for causing said indentator to controllably move vertically.

6. The apparatus of claim 1 wherein said loading means include electromagnetic means for moving said indentator, said electromagnetic means including a permanent magnet and a coil, said coil being within the magnetic field of said permanent magnet.

7. The apparatus of claim 6 further including a control unit, said loading means further including a lever, said coil being attached to one end of said lever, the other end of said lever being in motion-communicating relationship with said indentator, said control unit being adapted to control the current passing through said coil and thereby controlling the motion of said coil with respect to said permanent magnet.

8. The apparatus of claim 1 wherein said loading means include a piezoelectric element supported in motion-communicating relationship with said indentator.

9. The apparatus of claim 8 further including a control unit which is adapted to control the current passing through said piezoelectric element and thereby controlling the motion of said indentator.

10. The apparatus of claim 1 wherein said load-measuring means include a load cell.

11. The apparatus of claim 1 wherein said displacement-measuring means include a displacement sensor having a core rod.

12. A method of measuring interfacial shear strength between reinforcing fibers and a matrix of a composite material, said method comprising the steps of:
    applying different loads on selected one of said fibers by means of an indentator and measuring corresponding displacements of said indentator;
    calculating the square roots of values representing said displacements;
    obtaining a curve representing the relationship between said square roots and said loads;
    identifying a boundary point on said curve between a straight portion and a curving portion of said curve;

determining a load value $L_d$ corresponding to said boundary point; and calculating said interfacial shear strength by treating said value $L_d$ as the debonding load at which said fiber starts separating from said matrix.

13. The method of claim 12 further comprising the step of selecting said fiber from a sample of said composite material.

14. The method of claim 12 further comprising the step of measuring the diameter of said selected fiber.

15. The method of claim 14 wherein said measured diameter of said fiber is used in the calculation of said interfacial shear strength.

16. The method of claim 14 wherein the diameter of said fiber is measured by observing said fiber through a microscope and moving indicators in the field of vision of said microscope such that said indicators exactly sandwich said fiber therebetween.

17. The method of claim 12 wherein said interfacial shear strength is calculated by the formulas for debonding shear strength and sliding shear strength give below:

$$\tau_d = \alpha L_d / 2\pi R^2,$$

$$\tau_s = L_u^2 / (4\pi^2 R^3 E_f u)$$

where $\tau_d$ is the debonding shear strength, $\tau_s$ is the sliding shear strength, $$\alpha^2 = 2E_m / \{E_f(1+\nu_m)^2 \ln(1/\sqrt{B})\},$$

E is the elastic modulus, $\nu$ is the Poisson's ratio, R is the radius of the fiber, B is the bulk modulus of the fiber, and the subscripts m and f respectively refer to the matrix and the fibers, $L_u$ is a load value larger than said debonding load and u is the deviation of said curve from extrapolation of said straight portion at $L_u$.

* * * * *